United States Patent [19]

Ribier et al.

[11] Patent Number: 5,756,108
[45] Date of Patent: May 26, 1998

[54] OILY PHASE IN AN AQUEOUS PHASE DISPERSION STABILIZED BY CUBIC GEL PARTICLES AND METHOD OF MAKING

[75] Inventors: Alain Ribier; Bruno Biatry, both of Paris, France

[73] Assignee: L'Oreal, Paris, France

[21] Appl. No.: 555,784

[22] Filed: Nov. 9, 1995

[30] Foreign Application Priority Data

Nov. 10, 1994 [FR] France .................. 94 13564

[51] Int. Cl.⁶ .................. A61K 7/00; A01N 25/04
[52] U.S. Cl. .................. 424/401; 424/405; 424/70.1; 424/76.1; 424/61; 424/450; 514/939; 252/312
[58] Field of Search .................. 252/312; 514/939; 424/450, 401, 405, 70.1, 76.1, 61

[56] References Cited

U.S. PATENT DOCUMENTS

| | | | |
|---|---|---|---|
| 5,151,272 | 9/1992 | Engstrom et al. | 424/450 |
| 5,443,840 | 8/1995 | Morancais et al. | 424/450 |
| 5,531,925 | 7/1996 | Landh et al. | 424/450 |
| 5,569,663 | 10/1996 | Ribier et al. | 514/359 |
| 5,593,663 | 1/1997 | Leng et al. | 424/65 |

FOREIGN PATENT DOCUMENTS

WO 84/02076  6/1984  WIPO .

OTHER PUBLICATIONS

Simon Benita, Microencapsulation: Methods and Industrial Applications (Marcel Dekker, Inc., NY, NY, copyright 1996) pp. 415–417, 1996.
Sven Engström, "Drug Delivery From Cubic and Other Lipid–Water Phases"; Lipid Technology, vol. 2, No. 2, Apr. 1990, pp. 42–45.

*Primary Examiner*—Richard D. Lovering
*Assistant Examiner*—Daniel S. Metzmaier
*Attorney, Agent, or Firm*—Oblon, Spivak, McClelland, Maier & Neustadt, P.C.

[57] ABSTRACT

Composition in the form of a stable dispersion. This composition comprises:

(a) from 60 to 98% by weight of an aqueous phase, and (b) from 2 to 40% by weight of an oily phase, said oily phase being dispersed in said aqueous phase and stabilized using cubic gel particles, said particles being essentially formed of:

(i) 0.1 to 15% by weight, relative to the total weight of the composition, of at least one component selected from the group consisting of 3,7,11,15-tetramethyl-1,2,3-hexadecanetriol or phytanetriol, N-2-alkoxycarbonyl derivatives of N-methylglucamine and unsaturated fatty acid monoglycerides, and (ii) 0.05 to 3% by weight, relative to the total weight of the composition, of a dispersing and stabilizing agent, said agent being selected from the group consisting of surface-active agents which are water-soluble at room temperature, containing a linear or branched, saturated or unsaturated fatty chain having from 8 to 22 carbon atoms. Use in particular in the cosmetic, dermatological and pharmaceutical fields.

16 Claims, No Drawings

OILY PHASE IN AN AQUEOUS PHASE DISPERSION STABILIZED BY CUBIC GEL PARTICLES AND METHOD OF MAKING

The present invention relates to a composition in the form of a dispersion of an oily phase in an aqueous phase, the oily phase being stabilized by using cubic gel particles formed by using a water-soluble surface-active agent containing a fatty chain, and to a process for its preparation.

A large variety of products are in the form of a dispersion of an oily phase in an aqueous phase, such as in the form of an emulsion. Such is the case most particularly for cosmetic, dermatological or pharmaceutical products, these dispersions imparting good sensory properties to the skin and being easy to apply.

However, it is well known that dispersions, and in particular emulsions, lack stability over time, in particular on account of variations in temperature; these emulsions "break" giving rise to two separate phases, rendering them unusable.

The nature and the concentration of the emulsifying agent used may have a significant influence on the stability of such compositions.

However, it is well known that the choice and concentration of a suitable emulsifying agent will depend on various factors and, in particular, on the oil or oils constituting the oily phase of the dispersion or of the emulsion.

Moreover, it should be noted that certain surfactants are not free of drawbacks, in particular when they are employed at high concentration for the purpose of improving the stability.

Indeed, they may lead to certain irritation phenomena on sensitive skin.

It has now been observed, surprisingly and unexpectedly, that it is possible to obtain dispersions of an oily phase in an aqueous phase, which are particularly stable and non-irritant, using a very large variety of oils, by using cubic gel particles containing a low proportion of a water-soluble surface-active agent containing a fatty chain. The dispersions thus obtained moreover have particularly satisfactory sensory qualities.

The term cubic gel used according to the present invention denotes transparent gels which are isotropic in polarized light, in the form of a cubic liquid crystal phase. The cubic phases are organized in a bipolar manner into separate hydrophilic and lipophilic domains, in close contact and forming a thermodynamically stable three-dimensional network. Such an organization has been described in particular in "La Recherche", Vol. 23, pp. 306–315, March 1992 and in "Lipid Technology", Vol. 2, No. 2, pp. 42–45, April 1990. Depending on the arrangement of the hydrophilic and lipophilic domains, the cubic phase is said to be of normal or reverse type. The term "cubic gel" used in the present invention obviously groups together the gels having the various types of cubic phases.

The subject of the present invention is thus a composition in the form of a dispersion comprising:

(a) from 60 to 98% by weight of an aqueous phase, and
(b) from 2 to 40% by weight of an oily phase, said oily phase being dispersed in said aqueous phase and stabilized by using cubic gel particles, said particles being essentially formed of:
 (i) 0.1 to 15% by weight, relative to the total weight of the composition, of at least one component selected from the group consisting of 3,7,11,15-tetramethyl-1,2,3-hexadecanetriol or phytanetriol, N-2-alkoxycarbonyl derivatives of N-methylglucamine and unsaturated fatty acid monoglycerides, and (ii) 0.05 to 3% by weight, relative to the total weight of the composition, of a dispersing and stabilizing agent, said agent being selected from the group consisting of surface-active agents which are water-soluble at room temperature, containing a linear or branched, saturated or unsaturated fatty chain having from 8 to 22 carbon atoms.

According to a specific embodiment of the compositions according to the invention, the relative weight proportion of component (i) to the weight of the oily phase is between 0.02/1 and 1/1, and preferably between 0.05/1 and 0.5/1.

According to a specific embodiment of the compositions according to the invention, the relative weight proportion of component (i) to the weight of said dispersing and stabilizing agent is between 2 and 200, and preferably less than or equal to 50.

The phytanetriol of the cubic gel particles is a known compound, which is marketed in particular under the name "Phytanetriol-63926"® by the company Roche.

Among the N-2-alkoxycarbonyl derivatives of N-methylglucamine which may be mentioned in particular are those corresponding to the following formula (I):

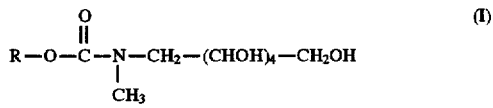

in which:

R represents a branched $C_6$–$C_{18}$ alkyl radical.

Among these derivatives, there may in particular be mentioned N-2-hexyldecyloxycarbonyl-N-methylglucamine, N-2-ethyl-hexyloxycarbonyl-N-methylglucamine and N-2-butyloctyloxycarbonyl-N-methylglucamine.

The compounds of formula (I) as defined above are novel and may be prepared according to a process comprising the steps consisting:

(a) in dissolving N-methylglucamine in a mixture of water and an organic solvent,
(b) in dispersing sodium bicarbonate in the mixture obtained above, at a suitable proportion corresponding approximately to four times the molar proportion of N-methylglucamine,
(c) in then introducing an alkyl chloroformate into the reaction mixture obtained, the alkyl radical being $C_6$–$C_{18}$, in a suitable proportion, generally in an equimolar proportion relative to that of N-methylglucamine, and then in allowing the mixture to react, and
(d) in recovering the N-2-alkoxycarbonyl derivative of N-methylglucamine formed.

The organic solvent used in step (a) is generally tetrahydrofuran.

Step (d) consists in filtering the reaction mixture obtained after step (c), in collecting the pasty residue by filtration and then in dissolving it in acetone so as to crystallize it at a temperature of the order of 5° C. After filtration, the crystals are drained and dried under vacuum. Examples of the preparation of certain N-2-alkoxycarbonyl derivatives of N-methylglucamine will be given below in the experimental section.

According to a specific embodiment of the compositions according to the invention, the cubic gel particles contain, as component (i), a mixture of phytanetriol in a proportion of from 1 to 40% by weight relative to the weight of the mixture, and of at least one N-2-alkoxycarbonyl derivative of N-methylglucamine of formula (I) in a proportion of from 60 to 99% by weight relative to the weight of the mixture.

According to a preferred form of this embodiment, the proportion of phytanetriol is from 10 to 30% by weight relative to the weight of the mixture, and that of the N-2-alkoxycarbonyl derivative of N-methylglucamine is from 70 to 90% by weight relative to the weight of the mixture.

The unsaturated fatty acid monoglycerides are preferably those having a $C_{16}$–$C_{22}$ unsaturated fatty chain.

Among these monoglycerides, there may in particular be mentioned glyceryl monooleate or monoolein and glyceryl monolinoleate or monolinolein.

It is, of course, possible to use, in the compositions according to the invention, a mixture of monoglycerides as defined above as well as a mixture of unsaturated fatty acid monoglycerides and saturated fatty acid monoglycerides, the proportion of saturated fatty acid monoglycerides preferably being, however, less than that of unsaturated fatty acid monoglycerides.

According to another embodiment of the compositions according to the invention, the cubic gel particles contain, as component (i), a mixture of phytanetriol in a proportion of from 1 to 50% by weight relative to the total weight of the mixture, and at least one unsaturated fatty acid monoglyceride in a proportion of from 50 to 99% by weight relative to the total weight of the mixture.

According to a preferred form of this embodiment, the proportion of phytanetriol is from 10 to 30% by weight relative to the weight of the mixture, and that of unsaturated fatty acid monoglyceride is from 70 to 90% by weight relative to the weight of the mixture.

The dispersing and stabilizing agent (ii) is preferably selected from the group consisting of:

(1) polyol alkyl or alkenyl ethers or esters, (2) N-acylated amino acids and derivatives thereof and peptides N-acylated with an alkyl or alkenyl radical, and salts thereof, (3) alkyl or alkenyl ether or ester sulphates, and the derivatives and salts thereof, (4) polyoxyethylenated alkyl or alkenyl fatty ethers or esters, (5) polyoxyethylenated alkyl or alkenyl carboxylic acids and salts thereof, (6) N-alkyl or N-alkenyl betaines, (7) alkyltrimethylammonium or alkenyltrimethylammonium and salts thereof, and (8) mixtures thereof.

In the compounds listed above, the alkyl and alkenyl radicals have from 8 to 22 carbon atoms and may be in the form of mixtures.

1—Polyol alkyl or alkenyl ethers or esters

Among these, there may in particular be mentioned:

(a) sorbitan alkyl or alkenyl esters polyoxyethylenated with at least 20 units of ethylene oxide, such as sorbitan palmitate 20 EO or Polysorbate 40 marketed under the name "Montanox 40 DF"® by the company Seppic, and sorbitan laurate 20 EO or Polysorbate 20 marketed under the name "Tween 20"® by the company ICI, (b) polyglyceryl alkyl or alkenyl esters containing at least 10 units derived from glycerol, which may or may not be oxyethylenated, such as polyglyceryl-10 laurate marketed under the name "Decaglyn 1-L"® by the company Nikko Chemicals, (c) polyglyceryl alkyl or alkenyl ethers, such as polyglyceryl-3 hydroxylauryl ether marketed under the name "Chimexane NF"® by the company Chimex, and (d) alkyl or alkenyl ethers or esters of mono- or polysaccharides such as those derived from glucose, fructose, galactose, maltose or lactose and especially the monoesters in positions -1 and -6 of D-fructose, of decylglucose and of decylpolyglucose.

2—N-Acylated amino acids and derivatives thereof and peptides N-acylated with an alkyl or alkenyl radical and salts thereof Among these, those for which the alkyl or alkenyl radical has at least 12 carbon atoms are preferably used.

According to the invention, the term amino acids refers to $\alpha$, $\beta$ or $\gamma$-amino acids. As N-acylated amino acid salts, there may for example be mentioned those of N-acylated glutamate such as monosodium cocoyl glutamate, monosodium lauroyl glutamate, disodium $C_{14}$–$C_{20}$ alkoyl glutamate (the $C_{14}$–$C_{20}$ alkoyl radical being derived from hydrogenated tallow), respectively marketed under the names "Acylglutamate CS-11"®, "Acylglutamate LS-11"® and "Acylglutamate HS-21"® by the company Ajinomoto.

There may also be mentioned N-acylated lysines such as lauroyllysine marketed under the name "Amihope LL"® by the company Ajinomoto.

The N-acylated amino acid derivatives and salts thereof are preferably N-acylated sarcosinates, such as sodium lauroyl sarcosinate marketed under the name "Oramix L30"® by the company Seppic, sodium myristoyl sarcosinate and sodium palmitoyl sarcosinate respectively marketed under the names "Nikkol Sarcosinate MN"® and "Nikkol Sarcosinate PN"®, by the company Nikko Chemicals.

Among the N-acylated peptides, there may be mentioned those derived from all or part of collagen or keratin, such as sodium lauroyl collagen and palmitoyl keratin marketed under the names "Proteol B 30"® and "Lipacide PK"® by the company Seppic.

3—Alkyl or alkenyl ether or ester sulphates, and the derivatives and salts thereof Among these, those for which the alkyl or alkenyl radical has at least 12 carbon atoms are preferably used.

Among the alkyl or alkenyl ether sulphates, the alkyl ether sulphate salts, and in particular sodium lauryl ether sulphate, are preferably used.

Among the alkyl or alkenyl ester sulphates, there may for example be mentioned the esters of isethionic acid and the salts thereof, and in particular sodium cocoyl isethionate marketed under the name "Geropon AC 78"® by the company Rhone Poulenc.

4—Polyoxyethylenated alkyl or alkenyl fatty ethers or esters

Among these, those for which the alkyl or alkenyl radical has at least 12 carbon atoms are preferably used. Those particularly preferred have at least 20 units of ethylene oxide, for example such as PEG-20 stearate, laureth-23, oleth-20 and PEG-25 phytosterol.

5—Polyoxyethylenated alkyl or alkenyl carboxylic acids and salts thereof

Among these, those containing at least 10 ethylene oxide units are preferably used, for example such as laureth-10 carboxylic acid and oleth-10 carboxylic acid.

6—N-alkyl or N-alkenylbetaines

Among these, those for which the alkyl or alkenyl radical has at least 12 carbon atoms are preferably used, for example such as laurylamidopropyl betaine and oleylamidopropyl betaine.

7—Alkyltrimethylammonium or alkenyltrimethylammonium and salts thereof

Among these, those for which the alkyl or alkenyl radical has at least 12 carbon atoms are preferably used. The bromides and chlorides, such as cocoyltrimethyl-ammonium chloride and cetyltrimethylammonium bromide, are preferably used as salts.

When the component (i) is an N-2-alkoxycarbonyl derivative of N-methylglucamine of formula (I), polyglyceryl-3 hydroxylauryl ether, sodium lauryl ether sulphate or cetyltrimethylammonium bromide is preferably used as dispersing and stabilizing agent (ii).

According to a specific embodiment of the compositions according to the invention, the cubic gel particles additionally comprise from 0.0005% to 5% by weight and preferably from 0.001% to 2% by weight of a water-insoluble ionic amphiphilic lipid.

Among these, there may in particular be mentioned:

(i) phospholipids such as natural phospholipids, for instance soya or egg lecithin, chemically or enzymatically modified phospholipids, for instance hydrogenated lecithin or phosphatidic acid sodium salt, and synthetic phospholipids such as dipalmitoylphosphatidylcholine, (ii) fatty acid phosphonic esters such as monocetyl phosphate and the sodium and potassium salts thereof, marketed under the name "Monafax 160"® by the company Mona, and dimyristyl phosphate and the sodium and potassium salts thereof, marketed under the name "Mexoryl SY"® by the company Chimex, (iii) N-acylated derivatives of glutamic acid, such as monosodium stearoyl glutamate marketed under the name "Acylglutamate HS 11"® by the company Ajinomoto and the monosodium cocoyl-($C_{14}$–$C_{20}$) alkoyl glutamate mixture, the $C_{14}$–$C_{20}$ alkoyl radical being derived from hydrogenated tallow, marketed under the name "Acylglutamate GS 11"® by the company Ajinomoto, (iv) sodium cetyl sulphate marketed under the name "Nikkol SCS"® by the company Nikko Chemicals, (v) sodium cocoyl monoglyceride sulphate marketed under the name "Nikkol SGC 80 N"® by the company Nikko Chemicals, and (vi) quaternary ammonium derivatives such as behenyltrimethylammonium chloride, dilauryldimethylammonium chloride, distearyldimethylammonium chloride and 4,5-dihydro-1-methyl-2-($C_{14}$–$C_{20}$) alkoyl-1-(2-($C_{14}$–$C_{20}$) alkoyl-aminoethyl) imidazolium methyl sulphate, the $C_{14}$–$C_{20}$ alkoyl radicals being derived from hydrogenated tallow, marketed under the name "Rewoquat W75H"® by the company Rewo Chemische, and dialkylhydroxyethylmethylanmonium methyl sulphate in which the alkyl radicals are derived from tallow, which may or may not be hydrogenated, marketed under the name "Stepanquat VP 85"® by the company Stepan and "Quaternium-82" marketed by the company Seppic under the name "Amonyl DM"®.

The incorporation of these water-insoluble ionic amphiphilic lipids imparts a surface charge to the cubic gel particles which causes mutual electrostatic repulsion of the particles.

The cubic gel particles as defined above generally have a mean size, measured using a BI 90 laser granulometer from the company Brookhaven Instruments Corporation, of approximately 0.05 µm to approximately 1 µm, and preferably of less than or equal to 0.5 µm.

It is also possible to incorporate into the cubic gel particles, various types of active compounds. In particular, the said particles may contain a hydrophilic active substance or a lipophilic active substance.

Obviously, by virtue of the specific structure of the cubic gel particles, it is possible to incorporate into the latter both hydrophilic active substances and lipophilic active substances even if there is a certain incompatibility between these active substances.

Among the various active substances which may be incorporated, there may in particular be mentioned:

1) antioxidants or anti-free-radical agents such as proteins and enzymes, for example superoxide dismutase (SOD), lactoperoxidase and lactoferrin; peptides and derivatives thereof such as taurine and carnosine; sequestering agents such as phytic acid and polyphosphonic derivatives; flavonoids such as rutin and α-glycosylrutin; chlorophylline; ethoxyquine; guanosine; tocopherols, in particular α-, β- or γ-tocopherols and in particular d-α-tocopherol marketed under the name "Copherol 1300"® by the company Henkel, as well as tocopherol acetate, di-t-butylhydroxybenzylidenecamphor marketed under the name "Mexoryl SAD"® by the company Chimex and t-butylhydroquinone marketed under the name "Embanox"® by the company Rhône-Poulenc; ascorbyl palmitate and β-carotene, 2) hydrating agents or humectants such as hyaluronic acid and the sodium salt thereof; β-glycerophosphate; glycerol and sorbitol, 3) UV screening agents such as the products marketed under the names "Eusolex 232"® by the company Merck, "Parsol 1789"® and "Parsol MCX"® by the company Givaudan-Roure, "Mexoryl SX"® by the company Chimex and "Uvinul T150"® by the company BASF, 4) keratolytic agents such as proteolytic enzymes and, in particular, subtilisin, trypsin, α-chymotrypsin and papain; retinoic acid and α-hydroxy acids, these being aromatic in particular, such as salicylic acid and derivatives thereof, in particular 5-n-dodecanoylsalicylic acid, 5) tanning accelerators such as caffeine, and tyrosine derivatives such as glucose tyrosinate and the N-L-malyltyrosine disodium salt, 6) depigmenting agents such as kojic acid, glycolic acid, vitamin C and especially magnesium ascorbyl phosphate, and arbutin and derivatives thereof, 7) natural dyes such as dyestuffs extracted from plants, such as chlorophyllin and β-carotene, or extracted from animals, such as cochineal carmine, and caramel, 8) tanning agents such as dihydroxyacetone, and indoles, 9) lipid regulators such as γ-orizanol, extract of *Centella asiatica* containing genin and asiatic acid, caffeine, and theophylline, 10) anti-ageing and anti-wrinkle agents such as hydroxy acids and, in particular, α-hydroxy acids such as glycolic acid, salicylic acid and derivatives thereof, such as n-octanoyl salicylic acid marketed under the name "Mexoryl SAB"® by the company Chimex, lactic acid and derivatives thereof such as glyceryl lactate stearate and glyceryl lactate palmitate which are marketed by the company Grinsted under the respective names "Lactodan B 30"® and "Lactodan F 15"®, and octyldodecyl lactate marketed under the name "Cosmol 13"® by the company Nisshin Oil Mills; retinol and derivatives thereof, such as retinol acetate, palmitate and propionate, and retinoids, 11) anti-inflammatory and cicatrizing agents such as 18-β-glycyrrhetinic acid and salts thereof, in particular such as the ammonium salt thereof, α-bisabolol, corticoids, and extract of *Centella asiatica*, 12) Antibacterial and antifungal agents such as benzalkonium chloride, chlorhexidine, hexetidine, and hexamidine,
13) insect repellents such as diethyl and dimethyl toluamides,
14) deodorants such as hexachlorophene, and triclosan, the product marketed under the name "Irgasan DP 300"® by the company Ciba-Geigy,
15) anti-dandruff agents such as octopirox, andpyridinethione derivatives such as those marketed under the names "Omadine"® by the company Olin,
16) agents for combating hair loss such as methyl or hexyl nicotinate, and minoxidil,
17) hair dyes such as oxidation couplers and bases, direct dyes, and auto-oxidizable dyes,
18) permanent-waving reducing agents such as thioglycolic acid, cysteine, cysteamine, N-acetylcysteine, N-acetylcysteamine, and glyceryl thioglycolate,
19) conditioners for skin and hair such as cationic polymers and cations, and
20) essential oils such as oil of bergamot.

In the compositions according to the invention, it is possible to use either cubic gel particles containing no active substances, or particles containing hydrophilic or lipophilic active substances, or alternatively, particles containing both hydrophilic and lipophilic active substances.

In the compositions according to the invention, the oily phase is dispersed in the aqueous phase and is generally in the form of droplets with a mean size of between 0.1 µm and 10 µm.

The oily phase of the compositions according to the invention consists essentially of at least one oil of plant, animal, mineral or synthetic origin, which is preferably cosmetically, dermatologically or pharmaceutically acceptable.

Among the plant oils which may be mentioned in particular are sunflower oil, corn oil, soya oil, marrow oil, grapeseed oil, blackcurrant seed oil, jojoba oil, sweet almond oil, safflower oil, sesame oil, borage oil, hazelnut oil, macadamia oil and the liquid fraction of karite butter.

Plant oils which may also be used are essential oils such as oil of eucalyptus, oil of hybrid lavender, oil of lavender, oil of vetiver, oil of Litsea cubeba, oil of lemon, oil of sandalwood, oil of rosemary, oil of camomile, oil of savory, oil of nutmeg, oil of cinnamon, oil of hyssop, oil of caraway, oil of orange, oil of geraniol, oil of prickly juniper and oil of bergamot.

Among the animal oils which may be mentioned in particular are fish oils, turtle oil, mink oil and hydrogenated squalene (or perhydrosqualene).

Mineral oils which may be mentioned in particular are liquid paraffin and isoparaffins.

Among the synthetic oils which may be mentioned in particular are hydrocarbons such as isohexadecane, polydecene and polyisobutene, fatty alcohols such as octyldodecanol, isostearyl alcohol and oleyl alcohol, esters such as essential fatty acid glycerides, triglycerides of capric and caprylic acids and mixtures thereof, and linear or branched fatty acid esters with fatty alcohols, such as purcellin oil (stearyl octanoate).

Synthetic oils which may also be used in the compositions according to the invention are silicone oils of linear type such as polydimethylsiloxane, of cyclic type such as cyclopentadimethylsiloxane, and of organically modified type such as polyphenyltrimethylsiloxane and polydimethylsiloxane, oxyethylenated or oxypropylenated.

There may also be mentioned fluoro oils such as perfluorodecahydronaphthalenes, for instance perfluorodecalin, as well as oils of polymeric type such as perfluoropolymethyl isopropyl ethers.

According to one embodiment of the compositions according to the invention, it is also possible to incorporate at least one active substance into the oily phase and/or into the aqueous phase. This active substance may be chosen in particular among the active substances as defined above.

The aqueous phase of the composition according to the invention may also contain various conventional additives. Among these, preserving agents, fragrances, pigments ($TiO_2$), dyestuffs, fillers and gelling agents may be mentioned in particular.

Among the gelling agents which may be used in the compositions according to the invention, there may be mentioned in particular cellulose derivatives such as hydroxyethyl cellulose and alkylhydroxyethyl celluloses, algae derivatives such as satia gum, natural gums such as tragacanth, synthetic polymers such as mixtures of polycarboxyvinyl acids and in particular those marketed under the names "Carbopol"® by the company Goodrich or "Synthalen"® by the company 3V SA.

The proportion of gelling agent is generally between 0.1 and 2% by weight relative to the total weight of the composition.

The subject of the present invention is also a process for the preparation of a composition in the form of a dispersion, this process consisting of at least two steps.

The first step consists in preparing an aqueous dispersion of cubic gel particles as defined above, by fragmentation, with a homogenizer, of a cubic gel formed by using at least one component (i) as defined above, water, optionally in the presence of water-insoluble ionic amphiphilic lipids and/or hydrophilic and/or lipophilic active substances and at least one dispersing and stabilizing agent (ii) as defined above. The homogenizer may be of the rotor-stator type with a high shear gradient, such as "Virtis"® or "Heidolph Diax 600"® or a high-pressure homogenizer operating between approximately 200 and 1800 bar (20 to 180 MPa).

The size of the cubic gel particles may be modified by the nature and concentration of the dispersing and stabilizing agent (ii) used.

It is, of course, possible to introduce various additives and/or active substances into the aqueous phase at this stage in the preparation of the aqueous dispersion of the cubic gel particles.

After formation of the cubic gel particles, the dispersing and stabilizing agent is generally outside the said particles.

The second step consists in then adding to the obtained dispersion an oily phase optionally containing certain lipophilic additives and/or active substances and in subjecting the mixture to mechanical stirring which may be performed in particular using a homogenizer of the same type as those defined above.

Various additives and/or active substances may also be introduced at this stage of the preparation.

In particular, when it is desired to prepare a gelled dispersion, an aqueous solution containing a gelling agent is generally added to the mixture obtained after the second step.

The compositions according to the invention in dispersion form are more particularly intended for cosmetic, dermatological or pharmaceutical use and are in various forms such as, in particular, a milk, a cream or a serum.

Examples of the preparation of N-2-alkoxycarbonyl derivatives of N-methylglucamine will now be given by way of illustration, along with several examples of compositions in dispersion form according to the invention.

EXAMPLES

Preparation of N-2-alkoxycarbonyl derivatives of N-methylglucamine

Example A

Preparation of N-2-hexyldecyloxycarbonyl-N methylglucamine

In a reactor, 70.2 g of N-methylglucamine (0.36 mol) are dissolved in a mixture consisting of 60 ml of water and 80 ml of tetrahydrofuran, and 120.96 g of sodium bicarbonate (1.44 mol) are then dispersed therein.

While maintaining the temperature of the reaction mixture at 8° C., 109.62 g of 2-hexyldecanoyl chloroformate (0.36 mol) are added dropwise and the mixture is left to react for 3 hours with stirring at 5° C. After the mixture has been left to stand overnight at room temperature, it is filtered and concentrated. The pasty residue is then dissolved in 1 liter of acetone. After crystallization by cooling, the product is filtered off and then recrystallized from 0.5 liter of acetone. The crystallized product is then filtered off and dried. 100 g of N-2-hexyldecyloxycarbonyl-N-methylglucamine are thus obtained (yield: 60%) with a melting point of: 70.6° C.

According to the same procedure as that described above, N-2-ethylhexyloxycarbonyl-N-methylglucamine (melting point: 74.2° C.) and N-2-butyloctyloxycarbonyl-N-methylglucamine (melting point: 77° C.) were also prepared.

EXAMPLES OF COMPOSITIONS

Example 1

An aqueous dispersion of cubic gel particles is obtained by mixing together 3 g of phytanetriol and 1.28 g of water, to which are added 75.7 g of an aqueous solution containing 0.95 g of Polysorbate 40 marketed under the name "Montanox 40 DF"® by the company Seppic. The mixture is then predispersed and homogenized, at room temperature, using a homogenizer of "Virtis"® type at 35,000 rpm for 5 minutes, this stirring being repeated 4 times.

To the aqueous dispersion of cubic gel particles obtained is then added 0.02 g of preserving agents, followed by an oily phase consisting of 10 g of apricot almond oil and 10 g of volatile silicone oil marketed under the name "Dow Corning Fluid 345"® by the company Dow Corning. After stirring at room temperature using a homogenizer of "Virtis"® type at 35,000 rpm for 5 minutes, this stirring being repeated 5 times, a stable dispersion of good consistency which is pleasant to apply is obtained.

The mean size of the droplets of the oily phase is approximately 0.51 μm (polydispersity factor: 0.6).

Example 2

An aqueous dispersion of cubic gel particles is obtained by mixing together 2.97 g of phytanetriol and 0.03 g of monosodium stearoylglutamate marketed under the name "Acylglutamate HS-11"® by the company Ajinomoto and 1.28 g of water, to which are added 75.7 g of an aqueous solution containing 0.95 g of Polysorbate 40. The mixture is then predispersed and homogenized, at room temperature, using a homogenizer of "Virtis"® type at 35,000 rpm for 5 minutes, this stirring being repeated 4 times.

To the aqueous dispersion of cubic gel particles obtained is then added 0.02 g of preserving agents, followed by an oily phase consisting of 10 g of apricot almond oil and 10 g of volatile silicone oil marketed under the name "Dow Corning Fluid 345"® by the company Dow Corning. After stirring at room temperature using a homogenizer of "Virtis"® type at 35,000 rpm for 5 minutes, this stirring being repeated 5 times, a stable and homogeneous dispersion is obtained.

The mean size of the droplets of the oily phase is approximately 0.37 μm (polydispersity factor: 0.05).

Examples 3, 4, 5 and 6 (Comparative)

The compositions below were prepared, taking the composition of Example 1 as reference and according to the same procedure:

| Example 3: | |
| --- | --- |
| Polysorbate 40 | 0.95 g |
| Preserving agents | 0.02 g |
| Apricot almond oil | 10 g |
| Volatile silicone oil marketed under the name "Dow Corning Fluid 345" ® by the company Dow Corning | 10 g |
| Water, qs | 100 g |
| Example 4: | |
| Polysorbate 40 | 0.95 g |
| Monosodium stearoylglutamate | 0.03 g |
| Preserving agents | 0.02 g |
| Apricot almond oil | 10 g |
| Volatile silicone oil marketed under the name "Dow Corning Fluid 345" ® by the company Dow Corning | 10 g |
| Water, qs | 100 g |
| Example 5: | |
| Monosodium stearoylglutamate | 0.03 g |
| Preserving agents | 0.02 g |
| Apricot almond oil | 10 g |
| Volatile silicone oil marketed under the name "Dow Corning Fluid 345" ® by the company Dow Corning | 10 g |
| Water, qs | 100 g |

The mean size of the lipid droplets in the dispersions obtained was then calculated by measurement using a BI90 laser granulometer from the company Brookhaven Instruments Corporation.

The stability of the dispersions obtained was also evaluated by macroscopic observation after 1 month at room temperature. A composition is considered to be stable when no separation of the aqueous and oily phases is observed after standing for 1 month.

The following results were obtained:

| Examples | Size of the lipid droplets | Stability after 1 month |
| --- | --- | --- |
| Example 1 | 0.51 μm | Stable |
| Example 3 | >1 μm | Unstable |
| Example 4 | >1 μm | Unstable |
| Example 5 | >2 μm | Unstable |

The dispersion of Example 3, which is unstable, differs from that of Example 1 only in the absence of cubic gel particles. This shows the importance of the latter for the good stability of the dispersion.

The dispersion of Example 4 is identical to that of Example 3 but contains a water-insoluble ionic amphiphilic lipid, namely monosodium stearoylglutamate. The presence of the latter has no effect on the stability, and this example again shows the importance of the cubic gel particles on the stability.

The dispersion of Example 5 is identical to that of Example 4 but contains no dispersing and stabilizing agent, namely Polysorbate 40. Here also, the lone presence of a water-insoluble ionic amphiphilic lipid does not make it possible to obtain a stable dispersion.

The result of this comparative study is that only the presence of cubic gel particles leads to dispersions having good stability.

Example 6: Day Cream

An aqueous dispersion of cubic gel particles is obtained by mixing together, at room temperature, 2.97 g of phytanetriol, 0.03 g of monosodium stearoylglutamate marketed under the name "Acylglutamate HS-11"® by the company Ajinomoto, 0.1 g of tocopherol acetate and 1.3 g of demineralized water, to which are added, at room temperature, 51 g of an aqueous solution containing 3 g of glycerol, 0.01 g of guanosine and 1 g of polysorbate 40.

The mixture is then dispersed and homogenized at room temperature using a homogenizer of "Heidolph Diax 600"® type fitted with an 18 G dispersion head, at 25000 rpm for 15 minutes, followed by 4 passages at 600 bar through a high-pressure homogenizer of "Soavi"® type.

To the aqueous dispersion of cubic gel particles obtained (referred to as dispersion A) is added a solution B obtained by mixing together the following ingredients:

| Solution B: | |
|---|---|
| Apricot almond oil | 12 g |
| Sunscreen | 1 g |
| Volatile silicone oil marketed under the name "Dow Corning Fluid 345" ® by the company Dow Corning | 12 g |
| Fragrance | 0.3 g |

The mixture is then homogenized to room temperature using a high-pressure homogenizer of "Soavi"® type, by 4 passages at 600 bar.

A solution C is then added thereto, this solution being obtained by mixing together the following ingredients:

| Solution C: | |
|---|---|
| Cetylhydroxyethyl cellulose marketed under the name "Natrosol Plus Grade 330 CS" ® by the company Aqualon | 1 g |
| Preserving agents | 0.3 g |
| Demineralized water | 18 g |

The mixture is then homogenized at room temperature using a paddle stirrer of "Heidolph RZR 50"® type, at 50 rpm for 30 minutes.

The dispersion obtained in the form of a cream is stable and homogeneous. It is easy to apply to the skin, is not sticky, and does not feel tacky, and protects the skin against the harmful effects of free radicals.

Example 7: Anti-ageing Day Cream

According to the same procedure as described in Example 6, a day cream was prepared in the form of a dispersion by mixing together the following parts:

| Dispersion A | |
|---|---|
| Phytanetriol | 2.97 g |
| Monosodium stearoylglutamate marketed under the name "Acylglutamate HS-11" ® by the company Ajinomoto | 0.03 g |
| Vitamin E | 0.1 g |
| Glycerol | 3 g |
| Polysorbate 40 marketed under the name "Montanox 40 DF" ® by the company Seppic | 1 g |
| Polyphosphonate marketed under the name "Dequest 2046" ® by the company Monsanto | 0.1 g |
| Superoxide dismutase marketed under the name "CU-ZN SOD" ® by the company Bio-Technology | 0.0005 g |
| Demineralized water | 44.4995 g |
| Solution B | |
| Blackcurrant seed oil | 10 g |
| Jojoba oil | 7 g |
| Vitamin E | 1 g |
| Volatile silicone oil marketed under the name "Dow Corning Fluid 345" ® by the company Dow Corning | 4 g |
| Sunscreen | 1 g |
| Fragrance | 0.3 g |
| Solution C | |
| Cetylhydroxyethyl cellulose marketed under the name "Natrosol Plus Grade 330 CS" ® by the company Aqualon | 1 g |
| Preserving agent | 0.3 g |
| Demineralized water | 23.7 g |

Example 8: Hydrating Milk

According to the same procedure as described in Example 6, a hydrating milk was prepared in the form of a dispersion by mixing together the following parts:

| Dispersion A | |
|---|---|
| Phytanetriol | 1.96 g |
| Cetyl phosphate marketed under the name "Monofax 160" ® by the company Mona | 0.04 g |
| Synthetic ceramide marketed under the name "Mexanyl GZ" ® by the company Chimex | 0.2 g |
| Glycerol | 2 g |
| L-Hydroxyproline | 1 g |
| Polysorbate 40 marketed under the name "Montanox 40 DF" ® by the company Seppic | 0.75 g |
| Polyethylene oxide containing 8 mol of ethylene oxide (PEG-8) | 1 g |
| Triethanolamine | 0.02 g |
| Demineralized water, qs | 61.58 g |
| Solution B | |
| Sweet almond oil | 5 g |
| Volatile silicone oil | 5 g |
| Fragrance | 0.3 g |
| Solution C | |
| Sodium hyaluronate | 0.05 g |
| Demineralized water | 10 g |

After homogenization of dispersion A and solutions B and C, solution D below was finally added:

| Solution D | |
|---|---|
| Mixture of polycarboxyvinyl acids marketed under the name "Carbopol 980" ® by the company Goodrich | 0.3 g |
| Preserving agents | 0.3 g |
| Triethanolamine qs | pH 6.5 |
| Demineralized water | 10.5 g |

Example 9: Day Fluid

| Dispersion A | |
|---|---|
| Phytanetriol | 0.27 g |
| N-2-hexyldecyloxycarbonyl-N-methylglucamine such as that obtained in Example A | 2.43 g |
| Lecithin marketed under the name "Epikuron 145 V" ® by the company Lucas Meyer | 0.3 g |
| Guanosine | 0.01 g |
| Glycerol | 3 g |
| Polyglyceryl-3 hydroxylauryl ether marketed under the name "Chimexane NF" ® by the company Chimex | 0.5 g |
| Demineralized water | 69.09 g |
| Solution B | |
| Apricot almond oil | 5 g |
| Sunscreen | 1 g |
| Volatile silicone oil | 5 g |
| Fragrance | 0.3 g |
| Solution C | |
| Mixture of polycarboxyvinyl acids marketed under the name "Carbopol 980" ® by the company Goodrich | 0.2 g |
| Preserving agents | 0.3 g |
| Triethanolamine qs | pH 6.5 |
| Demineralized water | 12.6 g |

Example 10: Day Cream

According to the procedure described in Example 6, a day cream is prepared in the form of a dispersion by mixing together the following parts:

| Dispersion A | |
|---|---|
| Phytanetriol | 0.3 g |
| Mixture of unsaturated fatty acid mono-glycerides marketed under the name "Myverol 18–99" ® by the company Eastman-Kodak | 2.55 g |
| Lecithin marketed under the name "Epikuron 200" ® by the company Lucas Meyer | 0.15 g |
| Glycerol | 3 g |
| L-Hydroxyproline | 1 g |
| D-Panthenol | 0.5 g |
| Polyphosphonate marketed under the name "Dequest 2046" ® by the company Monsanto | 0.1 g |
| Monosodium lauroylglutamate marketed under the name "Acylglutamate LS-11" ® by the company Ajinomoto | 0.1 g |
| Demineralized water | 56.85 g |
| Solution B | |
| Jojoba oil | 10 g |
| Di-t-butylhydroxybenzylidenecamphor marketed under the name "Mexoryl SAD" ® by the company Chimex | 0.05 g |
| Volatile silicone oil | 10 g |
| Fragrance | 0.3 g |
| Solution C | |
| Mixture of polycarboxyvinyl acids marketed under the name "Carbopol 980" ® by the company Goodrich | 0.4 g |
| Preserving agents | 0.3 g |
| Lysine, qs | pH 6.5 |
| Demineralized water | 14.4 g |

We claim:

1. A composition in the form of a dispersion for cosmetic, dermatological or pharmaceutical use containing in an aqueous phase a dispersion of an oily phase, said oily phase being present in a proportion of 2 to 40% by weight and being dispersed and stabilized by using cubic gel particles, said particles being essentially formed of: (i) 0.1 to 15% by weight relative to the total weight of the composition of at least one component selected from the group consisting of phytanetriol and N-2-alkoxycarbonyl derivative of N-methylglucamine having the formula:

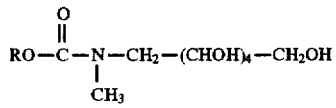

wherein

R represents a branched $C_6$–$C_{18}$ alkyl radical, and mixtures thereof, and (ii) 0.05 to 3% by weight relative to the total weight of the composition of a dispersing and stabilizing agent, said agent being a surface active substance, water-soluble at room temperature, containing a linear or branched, saturated or unsaturated, fatty chain having from 8 to 22 carbon atoms.

2. The composition according to claim 1, wherein the relative weight proportion of component (i) to the weight of the oily phase is between 0.02/1 and 1/1.

3. The composition according to claim 2, wherein said weight proportion is between 0.05/1 and 0.5/1.

4. The composition according to claim 1, wherein the relative weight proportion of component (i) to the weight of said dispersing and stabilizing agent is between 2 and 200.

5. The composition according to claim 1, wherein said N-2-alkoxycarbonyl derivative of N-methylglucamine is selected from the group consisting of N-2-hexyldecyloxycarbonyl-N-methylglucamine, N-2-ethylhexyloxycarbonyl-N-methylglucamine and N-2-butyloctyloxycarbonyl-N-methylglucamine.

6. The composition according to claim 1, wherein said cubic gel particles have a mean size from about 0.05 μm to 1 μm.

7. The composition according to claim 1, wherein said oily phase is in the form of droplets between 0.1 μm and 10 μm in size.

8. The composition according to claim 1, wherein said oily phase comprises at least one lipophilic active substance.

9. The composition according to claim 1, wherein said aqueous phase comprises at least one hydrophilic active substance.

10. The composition according to claim 1 wherein said dispersing and stabilizing agent is selected from the group consisting of:
   (1) polyol alkyl or alkenyl ethers or esters,
   (2) N-acylated amino acids, and peptides N-acylated with an alkyl or alkenyl radical and salts thereof,
   (3) alkyl or alkenyl ether or ester sulphates and salts thereof selected from the group consisting of sodium lauryl ether sulphate and sodium cocoyl isethionate,
   (4) polyoxyethylenated alkyl or alkenyl fatty ethers or esters,
   (5) polyoxyethylenated alkyl or alkenyl carboxylic acids and salts thereof,
   (6) N-alkyl or N-alkenyl betaines,
   (7) alkyl or alkenyltrimethylammonium and salts thereof selected from the group consisting of cocoyltrimethylammonium chloride, cetyltrimethylammonium bromide and salts thereof, and
   (8) mixtures thereof.

11. The composition according to claim 1 wherein said cubic gel particles contain at least one water-insoluble ionic amphiphilic lipid selected from the group consisting of:
   (i) phospholipids,
   (ii) fatty acid phosphoric esters and salts thereof,
   (iii) N-acylated compounds of glutamic acid selected from the group consisting of monosodium stearoyl glutamate and monosodium cocoyl ($C_{14}$–$C_{20}$) alkoyl glutamate, (iv) sodium cetyl sulphate, (v) sodium cocoyl monoglyceride sulphate, and (vi) quaternary ammonium compounds selected from the group consisting of behenyltrimethylammonium chloride, dilauryldimethylammonium chloride, distearyldimethylammonium chloride, and 4,5-dihydro-1-methyl-2-($C_{14}$–$C_{20}$) alkoyl-1-(2($C_{14}$–$C_{20}$) alkoyl aminoethyl) imidazolium methyl sulphate and dialkylhydroxyethylmethylammonium methyl sulphate.

12. The composition according to claim 11 wherein said water insoluble ionic amphiphilic lipid is present in a proportion between 0.001% to 2% by weight relative to the total weight of the composition.

13. The composition according to claim 1 wherein said cubic gel particles contain at least one active substance.

14. A process for the preparation of a composition in the form of a dispersion according to claim 1, said process consisting, in a first step, preparing an aqueous dispersion of cubic gel particles by fragmentation, with a homogenizer, of a cubic gel formed by at least one component (i) as defined in claim 1, water and at least one dispersing and stabilizing agent (ii) as defined in claim 1, and, in a second step, adding an oily phase to said obtained dispersion and subjecting the mixture to mechanical stirring.

15. The process according to claim 14, wherein the first step is performed in the presence of at least one water-insoluble ionic amphiphilic lipid and/or of at least one hydrophilic and/or lipophilic active substance.

16. The process according to claim 14, wherein the oily phase contains at least one lipophilic additive and/or active substance.

* * * * *